United States Patent
Momose

(10) Patent No.: US 10,473,498 B2
(45) Date of Patent: Nov. 12, 2019

(54) ELECTROMAGNETIC FLOW METER INCLUDING A FUNCTION OF MEASURING ELECTRICAL CONDUCTIVITY OF A FLUID

(71) Applicant: Azbil Corporation, Tokyo (JP)

(72) Inventor: Osamu Momose, Tokyo (JP)

(73) Assignee: Azbil Corporation, Tokyo (JP)

( * ) Notice: Subject to any disclaimer, the term of this patent is extended or adjusted under 35 U.S.C. 154(b) by 87 days.

(21) Appl. No.: 15/905,161

(22) Filed: Feb. 26, 2018

(65) Prior Publication Data

US 2018/0245956 A1    Aug. 30, 2018

(30) Foreign Application Priority Data

Feb. 27, 2017  (JP) ................. 2017-034923

(51) Int. Cl.
| | | |
|---|---|---|
| *G01F 1/58* | (2006.01) | |
| *G01F 1/60* | (2006.01) | |
| *G01N 27/04* | (2006.01) | |
| *G01N 27/08* | (2006.01) | |

(52) U.S. Cl.
CPC ............. *G01F 1/60* (2013.01); *G01F 1/588* (2013.01); *G01N 27/045* (2013.01); *G01N 27/08* (2013.01)

(58) Field of Classification Search
None
See application file for complete search history.

(56) References Cited

U.S. PATENT DOCUMENTS

| | | | |
|---|---|---|---|
| 2012/0031196 A1* | 2/2012 | Matzen ............. | G01F 1/60 73/861.12 |
| 2012/0036941 A1* | 2/2012 | Drahm .............. | G01F 1/58 73/861.12 |
| 2014/0260663 A1* | 9/2014 | Momose ........... | G01F 1/60 73/861.12 |

FOREIGN PATENT DOCUMENTS

| | | |
|---|---|---|
| JP | H05-172600 A | 7/1993 |
| JP | H07-005005 A | 1/1995 |
| JP | H08-261808 A | 10/1996 |

* cited by examiner

*Primary Examiner* — Harshad R Patel
(74) *Attorney, Agent, or Firm* — Amster, Rothstein & Ebenstein LLP

(57) ABSTRACT

An electromagnetic flow meter comprises a magnetic excitation coil, first and second electrodes which are disposed opposite to each other on an outer peripheral surface of a measurement tube, an amplifying circuit that amplifies an electromotive force generated between the first electrode and the second electrode, a flow rate calculation portion that calculates a flow rate of the fluid, a third electrode formed on the outer peripheral surface of the measurement tube separated from the first electrode and the second electrode, a fourth electrode which is in contact with the fluid, a resistor in which one end is connected to the third electrode, a voltage detecting portion that measures voltages of a signal generated in the third electrode by inputting an AC signal to the other end of the resistor, and an electrical conductivity calculating portion that calculates electrical conductivity of the fluid.

19 Claims, 8 Drawing Sheets

ELECTROMAGNETIC FLOW METER INCLUDING A FUNCTION OF MEASURING ELECTRICAL CONDUCTIVITY OF A FLUID

CROSS-REFERENCE TO RELATED APPLICATION

The present application claims the benefit of and priority to Japanese Patent Application No. 2017-034923, filed on Feb. 27, 2017, the entire contents of which are incorporated by reference herein.

TECHNICAL FIELD

The present invention relates to an electromagnetic flow meter for measuring a flow rate of a fluid in various process systems, in particular, to the electromagnetic flow meter having a function of measuring electrical conductivity of the fluid.

BACKGROUND ART

An electromagnetic flow meter is a measurement apparatus that includes a magnetic excitation coil for generating a magnetic field in a direction perpendicular to a flow direction of a fluid flowing in a measurement tube and a pair of electrodes disposed in the measurement tube and disposed in a direction orthogonal to the magnetic field generated by the magnetic excitation coil, and measures an electromotive force generated between the electrodes while alternately switching a polarity of an magnetic excitation current flowing to the magnetic excitation coil to measure a flow rate of a fluid to be detected flowing in the measurement tube.

In general, the electromagnetic flow meter is classified roughly into a contact type that measures the electromotive force of the fluid by directly contacting the electrode provided in the measurement tube with the fluid of a measurement target, and a capacitive type (non-contact type) that measures the electromotive force of the fluid through electrostatic capacitance between the fluid and the electrode without contacting the electrode provided in the measurement tube with the fluid of the measurement target.

The capacitive type electromagnetic flow meter calculates the flow rate by amplifying the electromotive force generated between the electrodes using a signal amplifying circuit (for example, differential amplifying circuit), then converting the amplified signal to a digital signal using an analog/digital conversion circuit, inputting the digital signal to a program processing device, such as a microcontroller, and executing predetermined arithmetic processing. In recent years, the capacitive type electromagnetic flow meter has particularly attracted attention since the electrode is difficult to deteriorate and maintenance is easy. As the related art of the capacitive type electromagnetic flow meter, for example, there are disclosures in PTL 1 and PTL 2.

Some electromagnetic flow meters have a function of measuring not only the flow rate of the fluid, but also electrical conductivity of the fluid (so-called conductivity). For example, PTL 3 discloses an electromagnetic flow meter including a two-electrode type electrical conductivity meter for obtaining the electrical conductivity by applying an AC signal, such as a sine wave or a square wave, between two electrodes and measuring a current flowing between the electrodes. In the electrical conductivity meter disclosed in PTL 3, two electrodes are immersed in a liquid of the measurement target at the same time to measure the electrical conductivity.

CITATION LIST

Patent Literature

[PTL 1] JP-A-5-172600
[PTL 2] JP-A-8-261808
[PTL 3] JP-A-7-5005

SUMMARY

The present inventor studies adding a function of measuring the electrical conductivity of the fluid to the capacitive type electromagnetic flow meter. However, according to the study of the present inventor, it becomes clear that there are the following problems.

In general, since the capacitive type electromagnetic flow meter is configured such that the fluid of the measurement target and the electrodes are not in contact with each other, an impedance between the fluid of the measurement target and the electrode increases. For this reason, when a noise is superimposed on an interconnection between the electrode and an input terminal of the signal amplifying circuit, there is a problem that measurement precision and measurement stability of the electromagnetic flow meter decrease. Therefore, in a typical capacitive type electromagnetic flow meter, a frequency of the magnetic excitation current is set to several tens Hz to several hundreds Hz, which is higher than that of a typical contact type electromagnetic flow meter.

On the other hand, in the electrical conductivity meter for measuring the electrical conductivity by immersing the two electrodes in the fluid (liquid) of a detection object at the same time, in general, a frequency of the AC signal applied between the two electrodes is set to several tens Hz to several hundreds Hz.

Accordingly, in a case where the capacitive type electromagnetic flow meter in the related art and the two-electrode type electrical conductivity meter in the related art are combined with each other, since the frequency bandwidth of the magnetic excitation current necessary for the measurement of the flow rate and the frequency bandwidth of the AC signal necessary for the measurement of the electrical conductivity overlap, the measurement precision and the measurement stability of the flow rate and the electrical conductivity may decrease due to mutual interference between the magnetic excitation current and the AC signal.

In the capacitive type electromagnetic flow meter in the related art, a common electrode which is in contact with the fluid of the measurement target and connected to a common potential, which is a reference for the flow rate measurement, is necessary in addition to the pair of electrodes disposed in the direction orthogonal to the magnetic field described above. For this reason, in the case where the electrical conductivity meter in the related art is combined with the capacitive type electromagnetic flow meter in the related art, since at least five electrodes are necessary around the measurement tube, there is a problem that it is difficult to miniaturize the electromagnetic flow meter. In particular, in the electromagnetic flow meter disclosed in PTL 3, since a ground ring connected to the common potential is provided between the electrode used for the measurement of the flow rate and the electrode used for the measurement of the electrical conductivity, the minimization of the electromagnetic flow meter becomes more difficult.

The present invention is made in view of the above problems, and a purpose of the present invention is to realize a small electromagnetic flow meter having higher measurement precision and measurement stability, and having an electrical conductivity measurement function.

An electromagnetic flow meter (100) comprises a measurement tube (1) formed of an electrical insulation material and through which a fluid of a measurement target flows, a magnetic excitation coil (Lex) disposed outside the measurement tube for generating a magnetic field according to a supplied AC current (Iex), a first electrode (11) and a second electrode (12) which are provided on an outer peripheral surface of the measurement tube and are disposed opposite to each other in a direction perpendicular to the magnetic field generated from the magnetic excitation coil, an amplifying circuit (13) that operates with a common potential (Vcom) as a reference and outputs a signal (VF) obtained by amplifying an electromotive force generated between the first electrode and the second electrode, a flow rate calculation portion (63) that calculates a flow rate of the fluid based on a signal output from the amplifying circuit, a third electrode (2) formed on the outer peripheral surface of the measurement tube separated from the first electrode and the second electrode, a fourth electrode (3) which is connected to the common potential and is in contact with the fluid, a resistor (R1) in which one end is connected to the third electrode, a voltage detecting portion (5) that measures voltages of a signal generated in the third electrode by inputting an AC signal to the other end of the resistor, and an electrical conductivity calculating portion (62) that calculates electrical conductivity of the fluid based on an amplitude of the voltages (VH and VL) measured by the voltage detecting portion.

In the electromagnetic flow meter, a frequency (f1) of the AC signal may be at least 100 times a frequency of the AC current supplied to the magnetic excitation coil.

In the electromagnetic flow meter, the amplifying circuit may comprise filters (131 and 132) for attenuating frequency components corresponding to the AC signal which are included in the signal obtained by amplifying the electromotive force.

The electromagnetic flow meter may further comprise a determining portion (64) that determines a presence or absence of the fluid in the measurement tube based on the electrical conductivity of the fluid calculated by the electrical conductivity calculating portion.

In the electromagnetic flow meter, the voltage detecting portion may comprise a first sample hold circuit (51) for sampling and holding a voltage of the third electrode in a first period (Tp) in which the AC signal has a first polarity and a second sample hold circuit (52) for sampling and holding a voltage of the third electrode in a second period (Tn) in which the AC signal has a second polarity opposite to the first polarity, and the electrical conductivity calculating portion (62) may calculate the electrical conductivity of the fluid based on the voltage (VH) sampled by the first sample hold circuit and the voltage (VL) sampled by the second sample hold circuit.

In the electromagnetic flow meter, the fourth electrode may be a pipe-shaped joint (3A) formed of a metal, of which one end is connected to the measurement tube and the other end is connectable to an external pipe.

The electromagnetic flow meter may still further comprise a shield cover (21) formed of a metal and disposed to face at least a part of the third electrode.

In the above description, as an example of configuration elements of the invention, reference numerals and signs on drawings corresponding to the configuration elements are described with parentheses.

According to the present invention, it is possible to realize a smaller electromagnetic flow meter having higher measurement precision and measurement stability, and having an electrical conductivity measurement function.

DETAILED DESCRIPTION

Hereinafter, an embodiment of the present invention will be described with reference to the drawings.

<Configuration of Electromagnetic Flow Meter According to the Embodiment>

Figure 1:
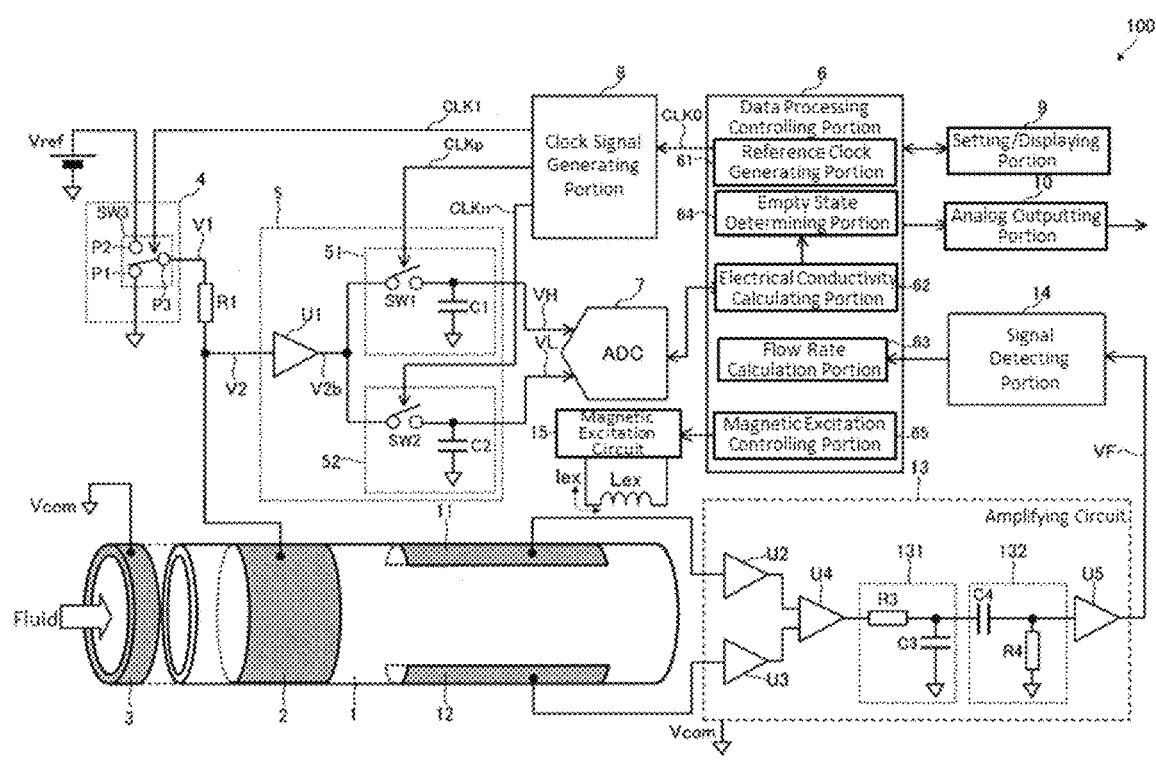
FIG. 1 is a diagram illustrating a configuration of an electromagnetic flow meter according to one embodiment of the present invention.

FIG. 1 is a diagram illustrating a configuration of an electromagnetic flow meter according to one embodiment of the present invention.

An electromagnetic flow meter 100 illustrated in the figure is a two-electrode type capacitive type electromagnetic flow meter having a function of measuring electrical conductivity of a fluid.

As illustrated in FIG. 1, the electromagnetic flow meter 100 comprises a measurement tube 1, a first electrode 11, a second electrode 12, a magnetic excitation coil Lex, a magnetic excitation circuit 15, a data processing controlling portion 6, an amplifying circuit 13, a signal detecting portion 14, a third electrode 2, a fourth electrode 3, an AC signal generation portion 4, a voltage detecting portion 5, an analog/digital converting portion (ADC) 7, a clock signal generating portion 8, a setting/displaying portion 9, and an analog outputting portion 10.

The electromagnetic flow meter 100 realizes a measurement of a flow rate of a fluid flowing in the measurement tube 1, and realizes measurement of the electrical conductivity of the fluid flowing in the measurement tube 1 using each function portion described above.

Hereinafter, each function portion will be described in detail separately for a flow rate measurement function of measuring the flow rate and an electrical conductivity measurement function of measuring the electrical conductivity.

(1) Flow Rate Measurement Function

The electromagnetic flow meter 100 measures the flow rate of the fluid flowing in the measurement tube 1 by supplying an AC current (hereinafter, refer to as "magnetic excitation current Iex") in which a polarity is switched alternately to the magnetic excitation coil Lex disposed such that a magnetic field generation direction is perpendicular to a flow direction of the fluid flowing in the measurement tube 1, and measuring an electromotive force generated between a pair of the first electrode 11 and the second electrode 12 disposed in the measurement tube 1 orthogonal to the generated magnetic field from the magnetic excitation coil Lex.

The flow rate measurement function is realized by the measurement tube 1, the magnetic excitation coil Lex, the magnetic excitation circuit 15, the first electrode 11, the second electrode 12, the data processing controlling portion 6, the amplifying circuit 13, the signal detecting portion 14, the setting/displaying portion 9, and the analog outputting portion 10.

The measurement tube 1 is a pipe through which the fluid of the measurement target (measurement target fluid) of the flow rate and the electrical conductivity flows. The measurement tube 1 is comprised of an electrical insulation material. As the electrical insulation material, it is preferable that a material has a relatively high electrical insulation property, for example, ceramic.

The magnetic excitation coil Lex is a component for generating the magnetic field with respect to the measurement tube 1 according to an applied magnetic excitation current Iex.

The magnetic excitation circuit 15 is a circuit for applying the magnetic excitation current Iex to the magnetic excitation coil Lex. In the magnetic excitation circuit 15, an output of the magnetic excitation current Iex is controlled by the data processing controlling portion 6.

The data processing controlling portion 6 is a function portion that performs an overall control of each function portion configuring the electromagnetic flow meter 100, and is comprised of, for example, a program processing device, such as a microcontroller and a CPU. Specifically, the data processing controlling portion 6 comprises a reference clock generating portion 61, an electrical conductivity calculating portion 62, a flow rate calculation portion 63, an empty state determining portion 64, and a magnetic excitation controlling portion 65. The function portions configuring the data processing controlling portion 6 are realized by, for example, controlling hardware resources configuring the program processing device according to a program.

The magnetic excitation controlling portion 65 is a function portion that generates the magnetic field in the measurement tube 1 by periodically switching the polarity of the magnetic excitation current Iex supplied to the magnetic excitation coil Lex by controlling the magnetic excitation circuit 15.

Here, a frequency of the magnetic excitation current Iex is several tens Hz to several hundreds Hz. Hereinafter, the frequency of the magnetic excitation current Iex is also referred to as "magnetic excitation frequency".

A detailed description of function portions other than the magnetic excitation controlling portion 65 in the data processing controlling portion 6 will be described below.

The first electrode 11 and the second electrode 12 are a pair of electrodes for measuring the electromotive force and which are comprised of a metal material. The first electrode 11 and the second electrode 12 are formed of a thin film-shaped metal material (for example, copper foil), and disposed opposite to each other in a direction perpendicular to the magnetic field generated from the magnetic excitation coil Lex in a partial region of an outer peripheral surface of the measurement tube 1. The first electrode 11, the second electrode 12, and the measurement tube 1 are joined by, for example, an adhesive. Since the measurement target fluid flows through the inside of the measurement tube 1, the first electrode 11 and the second electrode 12 are not in contact with the measurement target fluid. Hereinafter, the first electrode 11 is also referred to as "detecting electrode 11", and the second electrode 12 is also referred to as "detecting electrode 12".

The amplifying circuit 13 is a circuit that operates with a common potential Vcom as the reference, amplifies the electromotive force generated between the pair of detecting electrodes 11 and 12, and outputs the amplified signal as a flow rate signal VF.

The embodiment will be described on an assumption that the common potential Vcom is 0V (ground potential).

Specifically, the amplifying circuit 13 is configured to have preamplifiers U2 and U3, a differential amplifying circuit U4, a low-pass filter circuit 131, a high-pass filter circuit 132, and a buffer amplifier U5.

The preamplifier U2 is configured to have, for example, an operational amplifier or the like, and is a circuit that amplifies a voltage of the detecting electrode 11. The preamplifier U3 is configured to have, for example, the operational amplifier or the like, and is a circuit that amplifies a voltage of the detecting electrode 12. The differential amplifying circuit U4 is configured to have, for example, the operational amplifier or the like, and is a circuit that generates a differential signal according to a difference between the voltage amplified by the preamplifier U2 and the voltage amplified by the preamplifier U3.

The low-pass filter circuit 131 and the high-pass filter circuit 132 are circuits that attenuate predetermined frequency components included in the signal obtained by amplifying the electromotive force generated between the detecting electrode 11 and the detecting electrode 12. Here, the predetermined frequency components are frequency components corresponding to an AC signal V1 used for the measurement of the electrical conductivity described below.

The low-pass filter circuit 131 comprises, for example, a resistor R3 and a capacitor C3. The high-pass filter circuit 132 comprises, for example, a capacitor C4 and a resistor R4. The constants of the resistors R3 and R4, and the capacitors C3 and C4 configuring the low-pass filter circuit 131 and the high-pass filter circuit 132 are set to appropriate values for attenuating the predetermined frequency component described above.

The buffer amplifier U5 is configured to have, for example, the operational amplifier or the like, and is a circuit that buffers the differential signal output through the low-pass filter circuit 131 and the high-pass filter circuit 132 and outputs the buffered signal as the flow rate signal VF.

The signal detecting portion 14 is a function portion that measures the voltage of the flow rate signal VF output from the buffer amplifier U5, and supplies the measured voltage to the flow rate calculation portion 63 in the data processing controlling portion 6. Specifically, the signal detecting portion 14 samples and holds the voltage of the flow rate signal VF at a predetermined sampling period, converts the voltage (analog signal) to a digital signal, and supplies the digital signal to the flow rate calculation portion 63.

The flow rate calculation portion 63 calculates the flow rate of the fluid flowing in the measurement tube 1 based on the voltage of the flow rate signal VF measured by the signal detecting portion 14. Flow rate calculation processing by the flow rate calculation portion 63 is realized by, for example, a known flow rate calculation method in the capacitive type electromagnetic flow meter in the related art.

The setting/displaying portion 9 has a function of detecting a setting operation input of an operator and outputting the detected input to the data processing controlling portion 6, and a function of displaying a display output from the data processing controlling portion 6 using, for example, an LED or an LCD. For example, the operation input by the operator is detected, an execution of the flow rate measurement is instructed to the data processing controlling portion 6, and information on a flow rate measurement result by the data processing controlling portion 6 is displayed on the LED, the LCD, or the like.

The analog outputting portion 10 is a function portion for outputting an arithmetic result by the data processing controlling portion 6 to an external apparatus. Specifically, the analog outputting portion 10 outputs the arithmetic result by the data processing controlling portion 6 as an analog signal of 4 to 20 mA. For example, the information on the flow rate measurement result calculated by the flow rate calculation portion 63 is output as the analog signal of 4 to 20 mA.

With the function portions described above, the flow rate measurement function by the electromagnetic flow meter 100 is realized.

(2) Electrical Conductivity Measurement Function

The electromagnetic flow meter 100 measures the electrical conductivity of the fluid flowing in the measurement tube 1 by applying the AC signal to the third electrode 2 provided on the outer peripheral surface of the measurement tube 1 through a resistor R1, and measuring an amplitude of a signal V2 generated in the third electrode 2 at the time in a state where the fourth electrode 3, which is in contact with the fluid flowing in the measurement tube 1, is connected to the common potential Vcom.

The electrical conductivity measurement function is realized by the measurement tube 1, the third electrode 2, the fourth electrode 3, the AC signal generation portion 4, the voltage detecting portion 5, the data processing controlling portion 6, the analog/digital converting portion (ADC) 7, the clock signal generating portion 8, the setting/displaying portion 9, and the analog outputting portion 10.

The third electrode 2 is comprised of a metal material formed on an outer peripheral surface of the measurement tube 1. The third electrode 2 is formed of, for example, the thin film-shaped metal material (for example, copper foil), and extends in a circumferential direction of the measurement tube 1 in a partial region of the measurement tube 1 separated from the detecting electrodes 11 and 12. The third electrode 2 and the measurement tube 1 are joined by, for example, an adhesive. Since the measurement target fluid flows through the inside of the measurement tube 1, the third electrode 2 does not contact the measurement target fluid. Hereinafter, the third electrode 2 is also referred to as "non-contact electrode 2".

The fourth electrode 3 is an electrode which is connected to common potential Vcom and is in contact with the measurement target fluid. For example, as illustrated in FIG. 1, the fourth electrode 3 is comprised of a pipe-shaped metal material connected to the measurement tube 1. Hereinafter, the fourth electrode 3 is also referred to as "contact electrode 3".

The clock signal generating portion 8 is a circuit that generates a clock signal for controlling an operation timing of each function portion. Specifically, the clock signal generating portion 8 divides a reference clock signal CLK0 output from the reference clock generating portion 61 of the data processing controlling portion 6 described below to generate various clock signals CLK1, CLKp, and CLKn. Specific examples of the clock signals CLK1, CLKp, and CLKn will be described below.

The AC signal generation portion 4 is a circuit that generates an AC signal applied to the non-contact electrode 2. The AC signal generation portion 4 generates, for example, a pulse V1 as the AC signal. As illustrated in FIG. 1, for example, the AC signal generation portion 4 can be realized by a switch SW3 having a first terminal P1 connected to the common potential Vcom, a second terminal P2 connected to reference potential Vref (>Vcom), and a third terminal P3 connected to a resistor R1.

The switch SW3 switches a connection destination of the third terminal P3 between the first terminal P1 and the second terminal P2 in response to the clock signal CLK1 with a constant period output from the clock signal generating portion 8. As a result, a pulse V1 in which a low level voltage is the common potential Vcom, a high level voltage is the reference potential Vref, and a frequency f1 is the same as the clock signal CLK1 is output from the third terminal P3.

Here, it is desirable that the frequency f1 of the pulse V1 is at least 100 times a magnetic excitation frequency fex of the alternating magnetic excitation current Iex described above. A specific numerical range of the frequency f1 will be described below.

One end of the resistor R1 is connected to an output terminal (above-mentioned third terminal of switch SW3) of the AC signal generation portion 4, and the other end is connected to the non-contact electrode 2. As a result, the pulse V1 output from the AC signal generation portion 4 is input to the non-contact electrode 2 through the resistor R1.

The voltage detecting portion 5 is a circuit that measures a voltage of a signal V2 generated in the non-contact electrode 2. Specifically, the voltage detecting portion 5 measures a voltage of the signal V2 during a period Tp in which the pulse V1 has a first polarity (for example, high level (=Vref)), and measures a voltage of the signal V2 during a period in which the pulse V1 has a second polarity (for example, low level (=Vcom)) opposite to the first polarity.

More specifically, the voltage detecting portion 5 comprises, for example, a buffer amplifier U1 and sample hold circuits 51 and 52. The buffer amplifier U1 is comprised of, for example, an operational amplifier or the like, and buffers and outputs the signal V2 generated in the non-contact electrode 2. A voltage of a signal V2b output from the buffer amplifier U1 and the voltage of the signal V2 are substantially equal (V2b V2).

The sample hold circuits 51 and 52 are circuits for sampling and holding the voltage of the signal V2b output from the buffer amplifier U1 at a predetermined timing.

The sample hold circuit 51 comprises, for example, a switch SW1 in which one end is connected to an output terminal of the buffer amplifier U1 and a capacitor C1 connected between the other end of the switch SW1 and the common potential Vcom. For example, the switch SW1 is switched on/off in response to the clock signal CLKp. As a result, the sample hold circuit 51 can perform the sampling of the voltage of the signal V2b in response to the clock signal CLKp.

The sample hold circuit 52 comprises, for example, a switch SW2 of which one end is connected to the output terminal of the buffer amplifier U1 and a capacitor C2 connected between the other end of the switch SW2 and the common potential Vcom. For example, the switch SW2 is switched on/off in response to the clock signal CLKn. As a result, the sample hold circuit 52 can perform the sampling of the voltage of the signal V2b in response to the clock signal CLKn.

Figure 2:
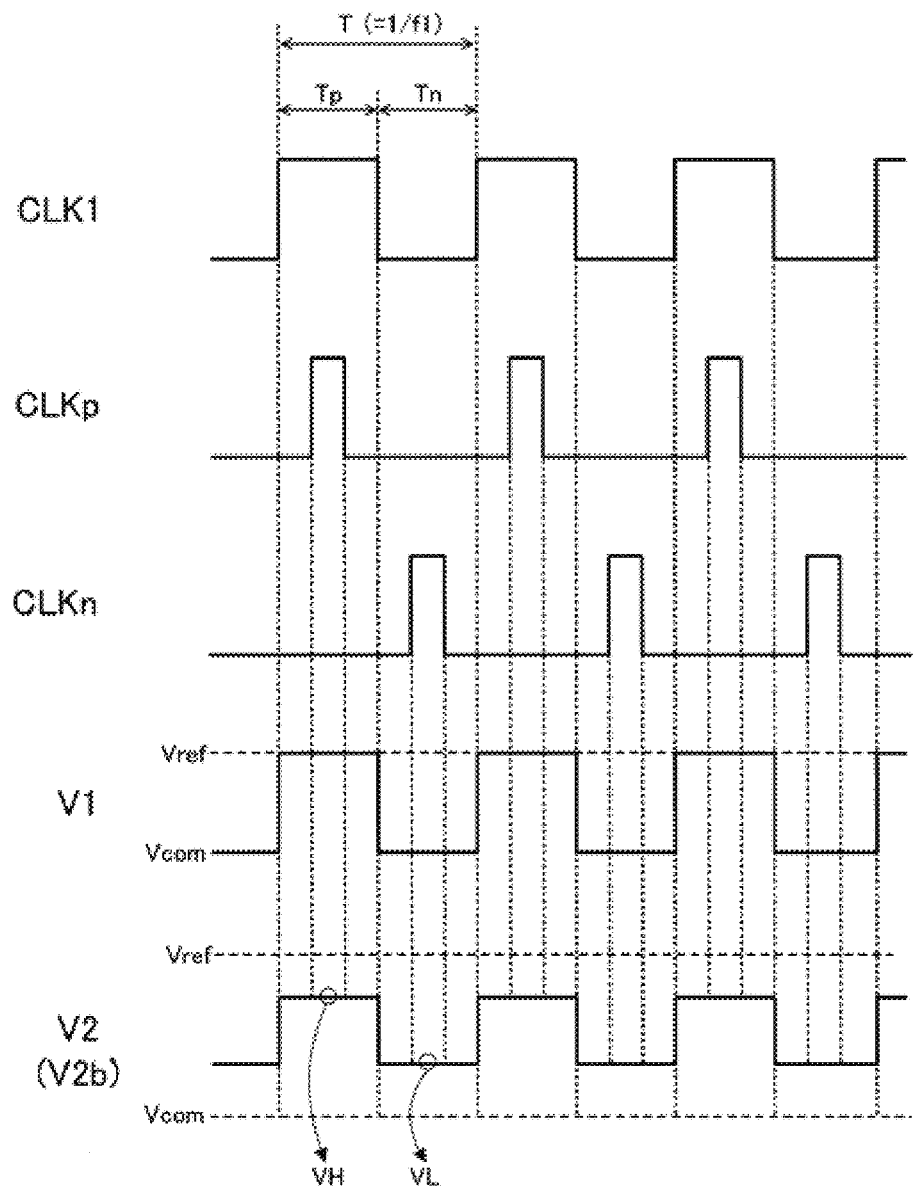
FIG. 2 is a timing chart diagram illustrating an operation timing of a voltage detecting portion.

FIG. 2 is a timing chart diagram illustrating an operation timing of a voltage detecting portion 5.

As illustrated in FIG. 2, the clock signal generating portion 8 generates a pulse with a period T (for example, duty ratio: 50%) as the clock signal CLK1, and provides the pulse to the AC signal generation portion 4. The AC signal generation portion 4 connects the third terminal P3 to the second terminal P2 (=Vref) when the clock signal CLK1 is at the high level, and connects the third terminal P3 to the first terminal P1 (=Vcom) when the clock signal CLK1 is at the low level. As a result, as illustrated in FIG. 2, the pulse V1, which becomes the reference potential Vref when the clock signal CLK1 is at the high level (first polarity) and becomes the common potential Vcom when the clock signal CLK1 is at the low level (second polarity), is output from the third terminal P3. The pulse V1 output from the third terminal P3 of the AC signal generation portion 4 is input to the non-contact electrode 2 through the resistor R1.

When the above-mentioned pulse V1 is output while the measurement target fluid flows through the inside of the measurement tube 1 and the contact electrode 3, a current flows into the common potential Vcom through the resistor R1, the non-contact electrode 2, the measurement target fluid, and the contact electrode 3. As a result, the signal V2 having a voltage according to the resistor R1 and an impedance on the other end side of the resistor R1 is generated in the non-contact electrode 2. At this time, as illustrated in FIG. 2, the signal V2 becomes a signal in which the voltage varies in synchronization with the pulse V1.

The clock signal generating portion 8 supplies a pulse which becomes the high level during the period Tp—in which the clock signal CLK1 is at the high level, that is, during the period in which the pulse V1 has the first polarity (for example, high level (=Vref))—to the sample hold circuit 51 as the clock signal CLKp.

The switch SW1 of the sample hold circuit 51 is turned on when the clock signal CLKp is at the high level, and turned off when the clock signal CLKp is at the low level. As a result, the sample hold circuit 51 samples a voltage VH when the signal V2 (V2b) generated in the non-contact electrode 2 becomes the high level.

Further, the clock signal generating portion 8 supplies a pulse which becomes the high level during the period Tn—in which the clock signal CLK1 is at the low level, that is, during the period when the pulse V1 has the second polarity (for example, low level (=Vcom))—to the sample hold circuit 52 as the clock signal CLKn.

The switch SW2 of the sample hold circuit 52 is turned on when the clock signal CLKn is at the high level, and turned off when the clock signal CLKn is at the low level. As a result, the sample hold circuit 52 samples a voltage VL when the signal V2 (V2b) generated in the non-contact electrode 2 becomes the low level.

The analog/digital converting portion 7 is a circuit that converts a voltage difference between the voltage VH obtained by the sample hold circuit 51 and the voltage VL sampled and held by the sample hold circuit 52 into a digital signal.

The reference clock generating portion 61 in the data processing controlling portion 6 is a function portion that generates a reference clock signal CLK0 supplied to the clock signal generating portion 8. The reference clock generating portion 61 can be realized by, for example, an oscillation circuit or the like that generates a signal using externally attached quartz crystal or ceramic oscillator.

The electrical conductivity calculating portion 62 in the data processing controlling portion 6 is a function portion that calculates the electrical conductivity of the measurement target fluid based on an amplitude of voltages measured by the voltage detecting portion 5. Specific processing contents by the electrical conductivity calculating portion 62 will be described below.

Further, the data processing controlling portion 6 comprises the empty state determining portion 64 that determines a presence or absence of the fluid in the measurement tube 1. The empty state determining portion 64 determines the presence or absence of the fluid in the measurement tube 1 based on the electrical conductivity calculated by the electrical conductivity calculating portion 62. For example, in a case where the electrical conductivity calculated by the electrical conductivity calculating portion 62 is smaller than a predetermined threshold value, the empty state determining portion 64 determines that there is no fluid in the measurement tube 1.

The setting/displaying portion 9, for example, detects an operation input by the operator, instructs the data processing controlling portion 6 to execute a measurement of the electrical conductivity and empty state determination processing, and displays information on a measurement result of the electrical conductivity by the data processing controlling portion 6 on the LED, the LCD, or the like. The analog outputting portion 10 outputs the information on the electrical conductivity calculated by the electrical conductivity calculating portion 62 and the Determination Result by the Empty State Determining Portion 64 as an Analog Signal of 4 to 20 mA.

<Calculation Principle of Electrical Conductivity>

Next, a calculation principle of the electrical conductivity in the electromagnetic flow meter 100 will be described.

As described above, in the state where the measurement target fluid flows through the inside of the measurement tube 1 and the contact electrode 3, when the pulse V1 is input to one end of the resistor R1, the current flows into the common potential Vcom through the resistor R1, the non-contact electrode 2, the measurement target fluid, and the contact electrode 3. A current path of the current can be represented by an equivalent circuit 200 illustrated in FIG. 3A.

Specifically, the equivalent circuit 200 is comprised of resistors R1 and Rb, capacitors Ca and Cb, and a signal source V1 that outputs the pulse V1. Here, Rb indicates a resistance value of the measurement target fluid, Ca indicates polarization capacitance between the contact electrode 3 and the measurement target fluid, and Cb indicates capacitance between the measurement target fluid and the non-contact electrode 2.

A value of the capacitor Cb between the measurement target fluid and the non-contact electrode 2 becomes small as compared with the two-electrode type electrical conductivity meter in the related art, in which the two electrodes are in contact with the measurement target fluid at the same time. For this reason, in order to measure a value of the resistor Rb of the measurement target fluid with high accuracy and with good reproducibility, it is desirable to make the frequency f1 of the pulse V1 as high as possible to minimize a reactance component due to the capacitor Cb with respect to the resistor Rb in the equivalent circuit 200.

Figure 3A:
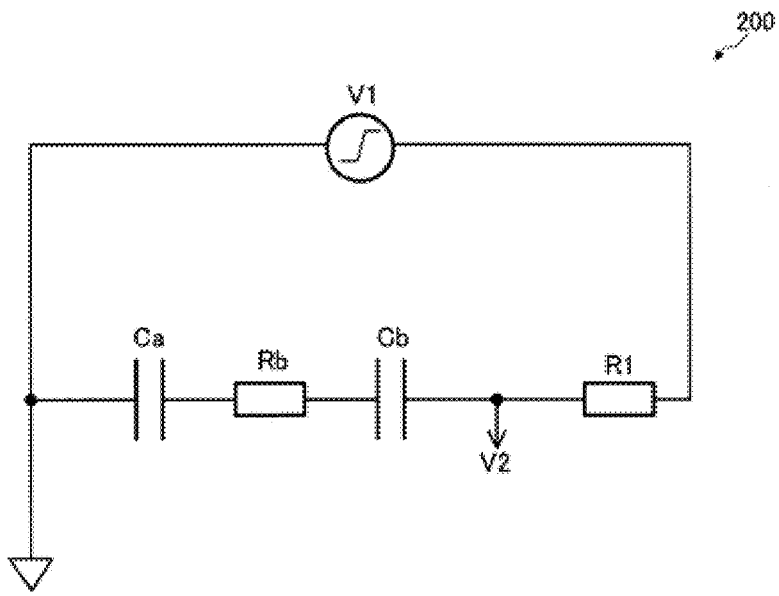
FIG. 3A is a diagram illustrating an equivalent circuit of a current path from a signal source V1 to common potential Vcom through a non-contact electrode 2.
Figure 3B:
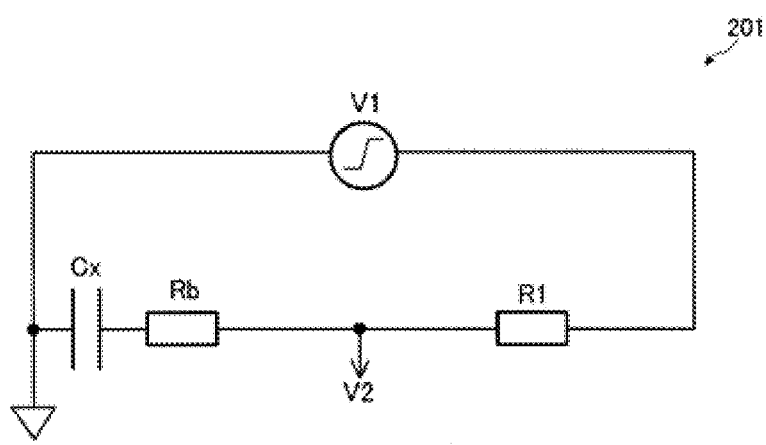
FIG. 3B is a diagram illustrating a simpler equivalent circuit of the current path from the signal source V1 to the common potential Vcom through the non-contact electrode 2.

In a case where the frequency f1 of the pulse V1 is increased to a level at which impedances of the capacitors Ca and Cb can be negligible, the equivalent circuit 200 can be redrawn in an equivalent circuit 201 illustrated in FIG. 3B. That is, the equivalent circuit 201 with the current path from the signal source V1 to the common potential Vcom through the non-contact electrode 2 can be represented by a signal V1 having an amplitude of ±Vref/2 with reference to a voltage Vref/2, a resistor voltage dividing circuit formed of a resistor R1 and a resistor Rb, and a coupling capacitor Cx.

In the equivalent circuit 201, a ratio of a voltage drop of the resistor R1 to a voltage drop of the resistor Rb during the period Tp in which the voltage of the signal V2 is at the high level is expressed by the following Equation (1). Here, Vr1_H represents a voltage across the resistor R1 during the period Tp in which the voltage of the signal V2 is at the high level, and Vrb_H represents a voltage across the resistor Rb during the period Tp in which the voltage of the signal V2 is at the high level.

[Math. 1]

$$Vr1\_H : Vrb\_H \approx \left\{ \frac{Vref}{2} - \left(VH - \frac{Vref}{2}\right)\right\} : \left(VH - \frac{Vref}{2}\right) \quad (1)$$
$$= (Vref - VH) : \left(VH - \frac{Vref}{2}\right)$$

In the equivalent circuit 201, a ratio of a voltage drop of the resistor R1 to a voltage drop of the resistor Rb during the period Tn in which the voltage of the signal V2 is at the low level is expressed by the following Equation (2). Here, Vr1_L represents a voltage across the resistor R1 during the period Tn in which the voltage of the signal V2 is at the low level, and Vrb_L represents a voltage across the resistor Rb during the period Tn in which the voltage of the signal V2 is at the low level. As described above, VH is a voltage when the signal V2b (V2) is at the high level, and VL is a voltage when the signal V2b (V2) is at the low level (refer to FIG. 2).

[Math. 2]

$$Vr1\_L : Vrb\_L \approx VL : \left(\frac{Vref}{2} - VL\right) \quad (2)$$

From the above Equations (1) and (2), a ratio between a voltage Vr1_HL, which is a sum of a voltage Vr1_H and a voltage Vr1_L, and a voltage Vrb_HL, which is a sum of a voltage Vrb_H and a voltage Vrb_L, is expressed by the following Equation (3).

[Math. 3]

$$Vr1\_HL : Vrb\_HL \approx \{Vref - (VH - VL)\} : (VH - VL) \quad (3)$$

From Equation (3), a ratio between the resistor R1 and the resistor Rb is expressed by the following Equation (4).

[Math. 4]

$$R1 : Rb\{Vref - (VH - VL)\} : (VH - VL) \quad (4)$$

From the above Equation (4), the resistor Rb is expressed by the following Equation (5).

[Math. 5]

$$Rb = \frac{R1 \times (VH - VL)}{Vref - (VH - VL)} \quad (5)$$

In the above Equation (5), both the reference potential Vref and the resistor R1 are known values. Accordingly, when a difference (VH−VL) between the voltage VH when the signal V2b (V2) is at the high level and the voltage VL when the signal V2b (V2) is at the low level, that is, an amplitude of the signal V2b (V2) is known, it is possible to obtain the resistor Rb of the measurement target fluid, that is, the electrical conductivity (=1/Rb) of the measurement target fluid based on Equation (5).

Figure 4:
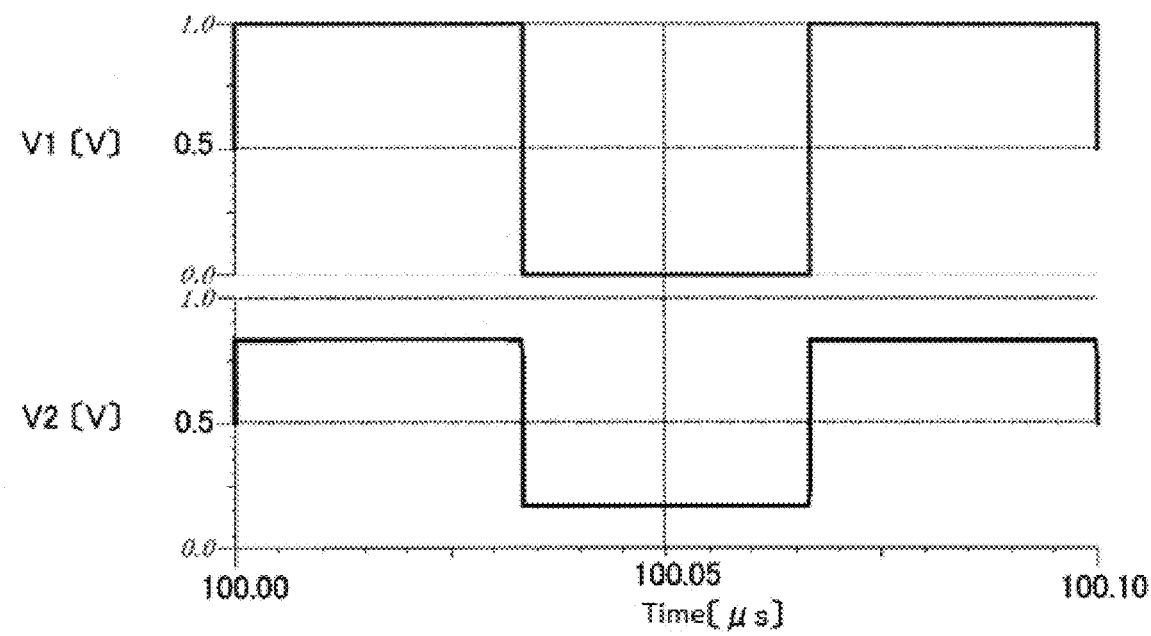
FIG. 4 is a diagram illustrating a simulation result of a signal V2 in the equivalent circuit 200 illustrated in FIG. 3A.

FIG. 4 is a diagram illustrating a simulation result of the signal V2 in the equivalent circuit 200 illustrated in FIG. 3A.

In the figure, in the equivalent circuit 200, the simulation result of the signal V2 is illustrated when R1=10 [kΩ], Rb=20 [kΩ], Ca=0.1 [μF], Cb=100 [pF], and a frequency and an amplitude of the pulse V1 are 15 [MHz] and 1 [V], respectively.

In the simulation result illustrated in FIG. 4, the voltage VH when the signal V2 is at the high level is about 0.8333V, and the voltage VL when the signal V2 is at the low level is about 0.1667V. Accordingly, in the case, the resistor Rb of the measurement target fluid is about 19.99 [Ω] from Equation (5).

In the electromagnetic flow meter 100 according to the embodiment, the electrical conductivity calculating portion 62 calculates the electrical conductivity of the measurement target fluid flowing through the measurement tube 1 by substituting the values of the voltages VH and VL input through the analog/digital converting portion 7 into Equation (5) described above.

As described above, in order to measure the value of the resistor Rb of the measurement target fluid with high accuracy and with good reproducibility, it is desirable to make the frequency f1 of the pulse V1 as high as possible to minimize the reactance component due to the capacitor Cb with respect to the resistor Rb. However, when the frequency f1 is set to be too high, the measurement precision of the resistor Rb of the measurement target fluid may decrease. Therefore, in a case of attempting to further improve the measurement precision and the reproducibility of the resistor Rb of the measurement target fluid, it is necessary to set the frequency f1 of the pulse V1 to an appropriate value. Hereinafter, description will be made in detail.

Figure 5:
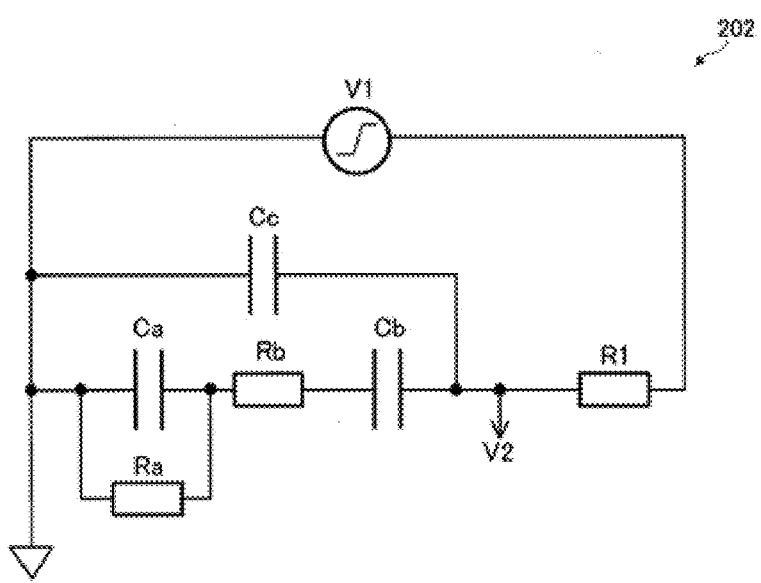
FIG. 5 is a diagram illustrating another equivalent circuit of the current path from the signal source V1 to the common potential Vcom through the non-contact electrode 2.

FIG. 5 is a diagram illustrating another equivalent circuit of the current path from the signal source V1 to the common potential Vcom through the non-contact electrode 2 in the electromagnetic flow meter 100.

As illustrated in an equivalent circuit 202 of the figure, a capacitor Cc between the contact electrode 3 and the non-contact electrode 2, and a polarization resistance Ra between the contact electrode 3 and the measurement target fluid actually exist in addition to the resistors R1 and Rb and the capacitors Ca and Cb between the signal source V1 generating the pulse V1 and the common potential Vcom. Here, Ca>>Cb>>Cc and Ra>>Rb.

When the frequency f1 of the pulse V1 is set to be too high, it is necessary to regard the current path between the signal source V1 and the common potential Vcom as the equivalent circuit 202 instead of the simple equivalent circuit 201 illustrated in FIG. 3B. For the reason, a waveform of a voltage applied to the resistor Rb is distorted due to the influence of the capacitor Cc, and the measurement precision of the resistor Rb may decrease.

Therefore, in order to suppress the decrease in the measurement precision of the resistor Rb due to the capacitor Cc, it is necessary to consider the influence of the impedance due to the capacitor Cb. Specifically, a reactance component Zcb (=1/(2πf1×Cb)) due to the capacitor Cb needs to satisfy a condition expressed by the following Equation (6).

[Math. 6]

$$\frac{Rb}{10} \leq Zcb \leq Rb \quad (6)$$

When Equation (6) is rewritten to an equation of the frequency f1, Equation (7) is obtained.

[Math. 7]

$$\frac{1}{2\times\pi\times Cb\times Rb} \leq f1 \leq \frac{10}{2\times\pi\times Cb\times Rb} \quad (7)$$

Accordingly, it is possible to suppress the decrease in the measurement precision of the fluid resistor (liquid resistor) Rb, that is, the electrical conductivity by setting the frequency f1 of the pulse V1 to a value within a range expressed by Equation (7).

Here, the capacitor Cb is determined by a relative permittivity of an electrical insulation material configuring mainly an area of the non-contact electrode 2 and the measurement tube 1, and it is possible to grasp the value of the capacitor Cb in advance since the influence of the polarization capacitance is so small as to be negligible.

For example, in Equation (7), when Rb=10 [kΩ] and Cb=100 [pF], the frequency f1 of the pulse V1 is in a range of about 160 kHz to 1600 kHz.

In this case, it is desirable that the magnetic excitation frequency fex is set to a value in a range of about 1.6 kHz to 16 kHz or less. As a result, it is possible to make the frequency bandwidth of the magnetic excitation current Iex according to the flow rate measurement function different from the frequency bandwidth of the AC signal (pulse V1) according to the electrical conductivity measurement function.

Figure 6A:
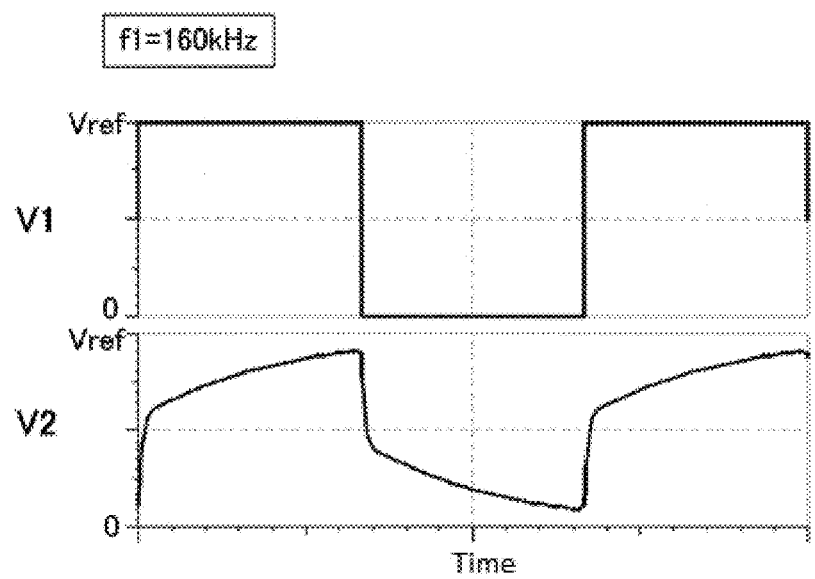
FIG. 6A is a diagram illustrating a simulation waveform of a signal V2 in a case where a frequency f1 of a pulse V1 is 160 kHz in the equivalent circuit 202 illustrated in FIG. 5.
Figure 6B:
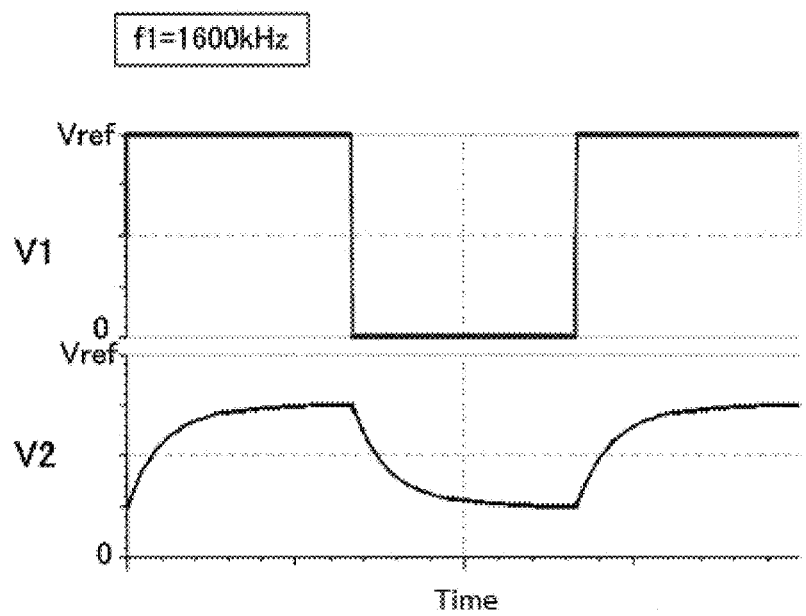
FIG. 6B is a diagram illustrating a simulation waveform of the signal V2 in a case where the frequency f1 of the pulse V1 is 1600 kHz in the equivalent circuit 202 illustrated in FIG. 5.

FIGS. 6A and 6B illustrate simulation results when the frequency f1 of the pulse V1 is set to a value in the range of 160 kHz to 1600 kHz. FIG. 6A is a diagram illustrating a simulation waveform of the signal V2 in a case where the frequency f1 of the pulse V1 is 160 kHz in the equivalent circuit 202, and FIG. 6B is a diagram illustrating a simulation waveform of the signal V2 in a case where the frequency f1 of the pulse V1 is 1600 kHz in the equivalent circuit 202. In the simulation, Ra=1 [MΩ], Rb=10 [kΩ], Ca=0.1 [uF], Cb=100 [pF], and Cc=10 [pF].

As described above, in the case of attempting to improve the measurement precision and the reproducibility of the resistor Rb of the measurement target fluid, the frequency f1 of the pulse V1 may be set to an appropriate range (Equation (7)) considering the equivalent circuit 202.

However, even in the case where the frequency f1 of the pulse V1 may be set to the appropriate range, since the current path between the signal source V1 and the common potential Vcom cannot be completely regarded as the simple equivalent circuit 201 illustrated in FIG. 3B, some error may occur in a calculation method based on Equation (5).

Figure 7:
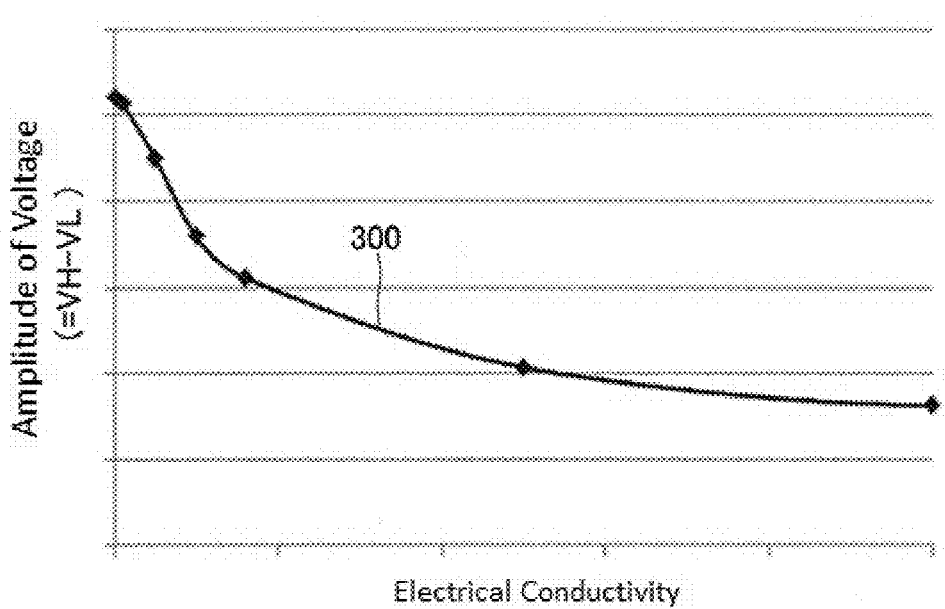
FIG. 7 is a diagram illustrating a relationship between an amplitude (VH−VL) of the signal V2 and electrical conductivity of a measurement target fluid.

For example, in the equivalent circuit 202 illustrated in FIG. 5, a relationship between the amplitude (VH−VL) of the signal V2 and the electrical conductivity of the measurement target fluid is represented by, for example, a non-linear characteristic 300 illustrated in FIG. 7.

Therefore, in the case of attempting to further improve the measurement precision and the reproducibility of the resistor Rb of the measurement target fluid, the electrical conductivity may be calculated using a look-up table created in advance indicating a correspondence relationship between the amplitude (VH−VL) of the signal V2 and the electrical conductivity of the measurement target fluid.

For example, a test is performed in advance to examine the relationship between the amplitude (VH−VL) of the signal V2 and the electrical conductivity of the measurement target fluid using a fluid (liquid) in which the electrical conductivity is known, and a look-up table indicating the correspondence relationship between the amplitude (VH−VL) of the signal V2 and the electrical conductivity of the measurement target fluid is created based on the test result. The created look-up table is stored in, for example, a storing portion, such as a non-volatile memory, in the program processing device, such as a microcontroller functioning as the data processing controlling portion 6.

When the electrical conductivity of the measurement target fluid is calculated, the electrical conductivity calculating portion 62 refers to the look-up table stored in the storing portion and reads a value of the electrical conductivity corresponding to the value of the amplitude (VH−VL) calculated from the values of the voltages VH and VL input through the analog/digital converting portion 7 to calculate the electrical conductivity of the measurement target fluid.

According to this, it is possible to further improve the measurement precision and the reproducibility of the resistor Rb of the measurement target fluid.

Next, a realization example of the electromagnetic flow meter 100 is illustrated.

Figure 8:
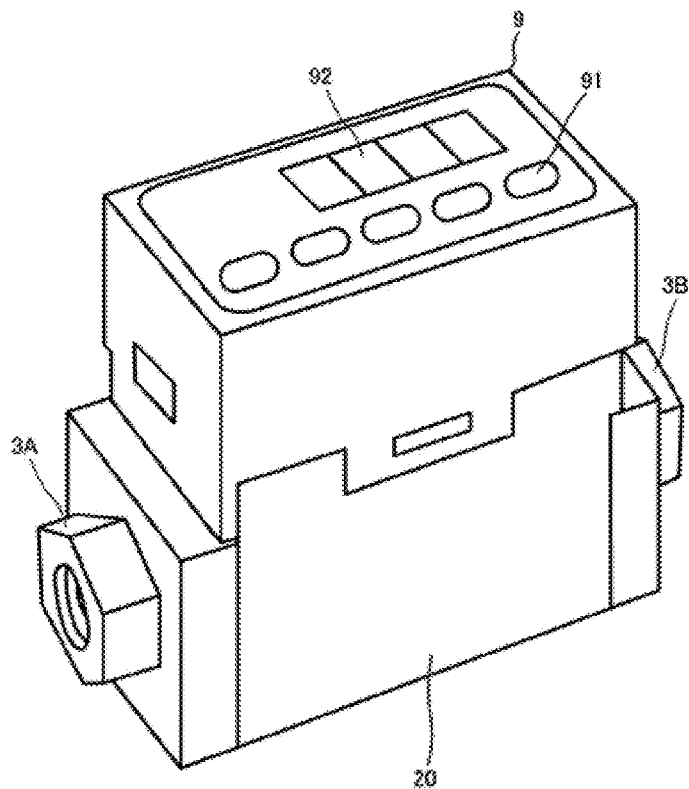
FIG. 8 is a perspective view illustrating a realization example of the electromagnetic flow meter 100 according to an embodiment.

FIG. 8 is a perspective view illustrating the realization example of the electromagnetic flow meter 100 according to the embodiment.

As illustrated in the figure, the electromagnetic flow meter 100 is realized by accommodating the measurement tube 1, the non-contact electrode 2, and the contact electrode 3, and a printed circuit board on which electronic circuits and the like such as the AC signal generation portion 4, the voltage detecting portion 5, the data processing controlling portion 6, the analog/digital converting portion 7, the clock signal generating portion 8, and the analog outputting portion 10 are formed in a casing 20 formed of a metal, a resin, or the like, and by covering an opening portion of the casing 20 with the setting/displaying portion 9.

The setting/displaying portion 9 comprises an operating button 91 for realizing the function of detecting the setting operation input by the operator and outputting the detected input to the data processing controlling portion 6, and a display device 92 such as the LED or the LCD for realizing the function of displaying the display output from the data processing controlling portion 6.

In a pair of facing side surfaces of the casing 20, pipe-shaped joints 3A and 3B comprised of a metal material (for example, SUS) capable of connecting a pipe (not illustrated) provided outside the electromagnetic flow meter 100 and the measurement tube 1 are disposed.

Figure 9A:
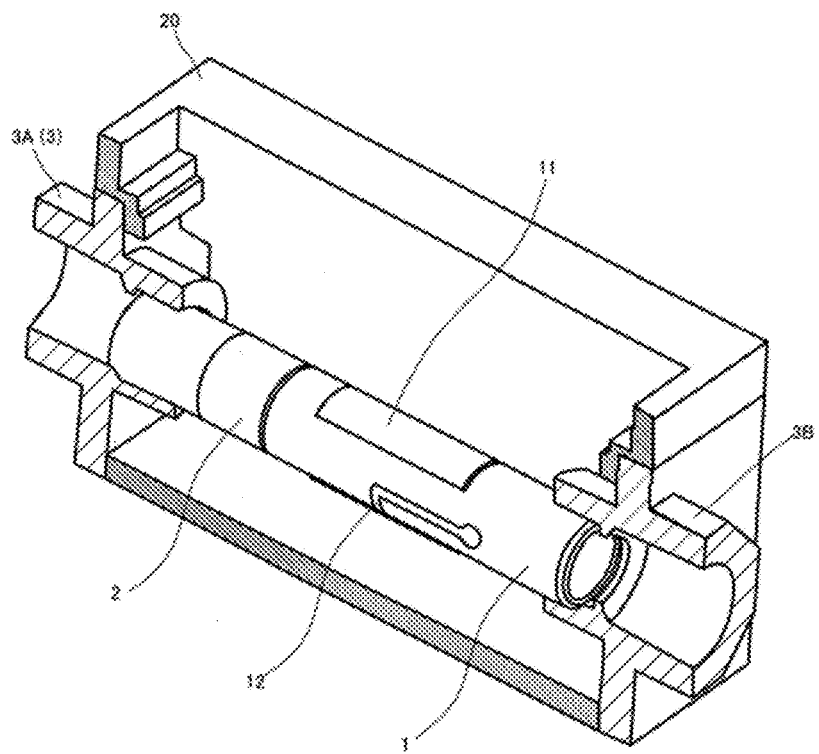
FIG. 9A is a cross-sectional perspective view illustrating the inside of a casing 20.
Figure 9B:
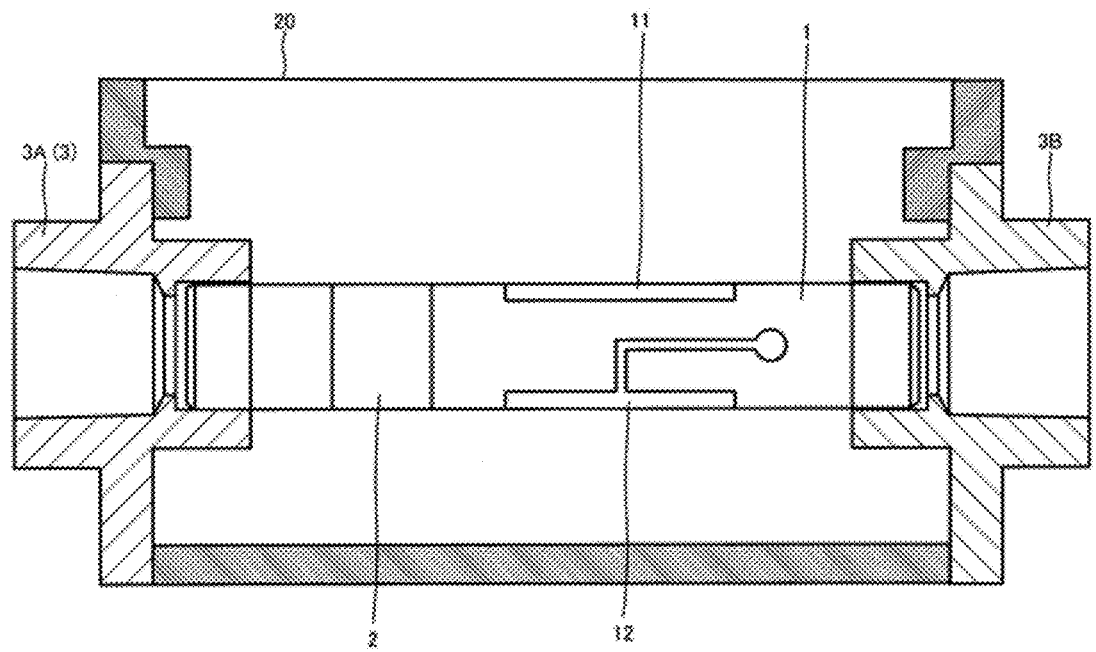
FIG. 9B is a cross-sectional front view illustrating the inside of the casing 20.

FIG. 9A is a cross-sectional perspective view illustrating the inside of the casing 20, and FIG. 9B is a cross-sectional front view illustrating the inside of the casing 20.

As illustrated in FIGS. 9A and 9B, the measurement tube 1 is disposed in the casing 20 along the longitudinal direction of the casing 20. The joint 3A and the joint 3B are connected respectively to both end portions of the measurement tube 1.

Here, one of two joints 3A and 3B functions as the contact electrode 3. For example, the joint 3A not only connects an external pipe to the measurement tube 1, but also functions as the contact electrode 3 by being connected to the common potential Vcom. In this case, the non-contact electrode 2 is formed on an outer peripheral surface near the end portion to which the joint 3A is connected in the measurement tube 1.

The detecting electrodes 11 and 12 for the flow rate measurement are formed on a region between the non-contact electrode 2 and the joint 3B in the outer peripheral surface of the measurement tube 1.

As described above, an area of the contact electrode 3 in contact with the measurement target fluid is widened by realizing the contact electrode 3 with the joint 3A formed of the metal. As a result, even in the case where the adhesion of foreign matter or the corrosion occurs in the contact electrode 3, since the area of a portion in which the adhesion of the foreign matter or the corrosion occurs is relatively small with respect to the entire area of the contact electrode 3, it is possible to suppress the measurement error due to the change in the polarization capacitance.

Figure 10A:
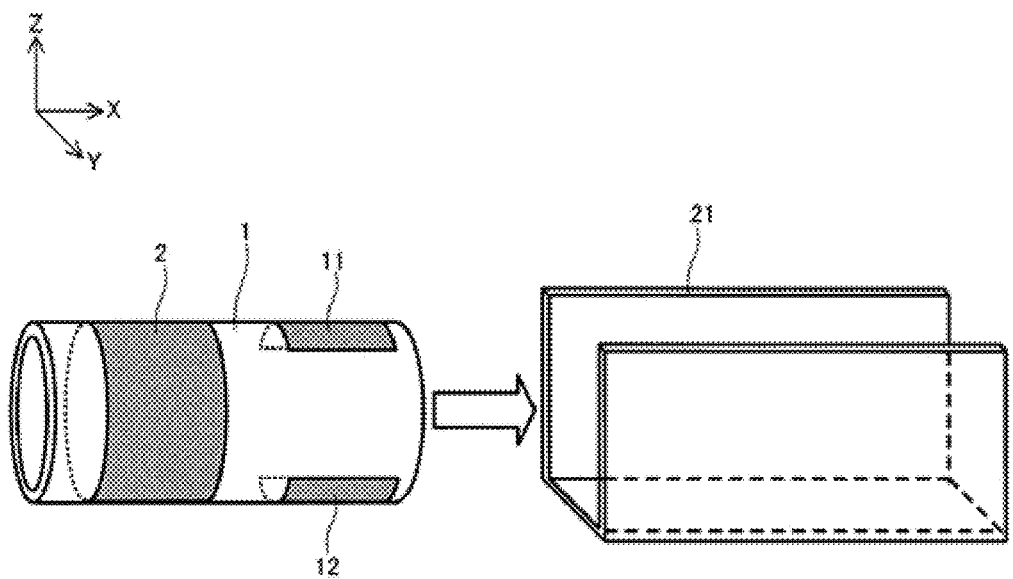
FIG. 10A is a perspective view illustrating a disposition example of a shield cover.

On the other hand, it is desirable that the non-contact electrode 2 is surrounded by, for example, a shield cover 21 formed of a metal connected to the common potential Vcom. For example, as illustrated in FIG. 10A, the measurement tube 1 is disposed such that the non-contact electrode 2 is surrounded by the shield cover 21 in the casing 20. According to this, it is possible to reduce an electromagnetic wave noise radiated from the non-contact electrode 2 to the outside of the casing 20.

Figure 10B:
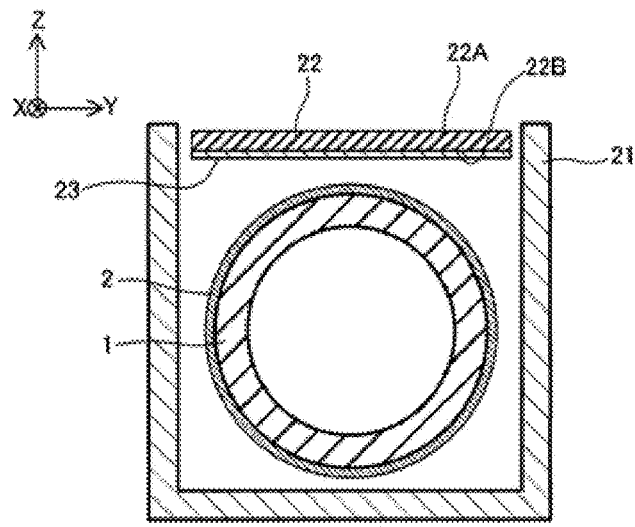
FIG. 10B is a side view illustrating the disposition example of a shield cover.

Here, the shield cover 21 may be disposed to face at least a part of the non-contact electrode 2. For example, as illustrated in FIG. 10B, the shield cover 21 may be formed in a U shape in a side view, and a printed circuit board 22 on which the electronic circuits and the like configuring the AC signal generation portion 4, the data processing controlling portion 6, and the like described above are formed on a principal surface 22A may be disposed on an opening side of the shield cover 21. In the case, a metal solid pattern 23 is formed entirely on a principal surface 22B opposite to the principal surface 22A of the printed circuit board 22.

According to this, it is easy to route signal lines connecting the AC signal generation portion 4 and the voltage detecting portion 5 disposed on the printed circuit board 22 with the non-contact electrode 2, and it is possible to reduce the electromagnetic wave noise radiated from the signal lines to the outside of the casing 20 since most of the signal lines can be disposed in the shield cover 21.

The shield cover 21 may be disposed to face at least a part of not only the non-contact electrode 2, but also the detecting electrodes 11 and 12 for the flow rate measurement. According to this, electromagnetic wave noise that the detecting electrodes 11 and 12 receive from the outside of the casing 20 can be reduced.

<<Effect of Electromagnetic Flow Meter 100 According to the Embodiment>>

Since the electromagnetic flow meter 100 according to the embodiment is realized by the non-contact electrode 2 in which one electrode of the two electrodes necessary for the measurement of the electrical conductivity is not in contact with the measurement target fluid, it is necessary to increase the frequency of the AC signal applied between both electrodes as compared with the two-electrode type electrical conductivity meter in the related art, in which the two electrodes are in contact with the fluid at the same time. For this reason, in the electromagnetic flow meter 100, since the frequency bandwidth of the magnetic excitation current necessary for the measurement of the flow rate is different from the frequency bandwidth of the AC signal (pulse V1) necessary for the measurement of the electrical conductivity, it is possible to prevent the magnetic excitation current and the AC signal from interfering with each other. As a result, it is possible to prevent the decrease of the measurement precision and the measurement stability of the flow rate and the electrical conductivity in the case of adding the electrical conductivity measurement function to the capacitive type electromagnetic flow meter.

In the electromagnetic flow meter 100 according to the embodiment, since the other electrode (contact electrode 3) of the two electrodes necessary for the measurement of the electrical conductivity described above is in contact with the measurement target fluid and is connected to the common potential, it is possible to reduce the number of electrodes around the measurement tube 1 as compared with a case where the electrical conductivity meter in the related art is incorporated simply in the capacitive type electromagnetic flow meter in the related art. That is, in the electromagnetic flow meter 100 according to the embodiment, since the contact electrode 3 used for the measurement of the electrical conductivity also serves as a common electrode used for the flow rate measurement, the number of necessary electrodes can be reduced. As a result, it is possible to miniaturize the electromagnetic flow meter having the electrical conductivity measurement function.

Accordingly, with the electromagnetic flow meter 100 according to the embodiment, it is possible to realize a small electromagnetic flow meter having high measurement precision and measurement stability, and having the electrical conductivity measurement function.

With the electromagnetic flow meter 100 according to the embodiment, it is possible to form the detecting electrodes 11 and 12 for the measurement of the flow rate and the non-contact electrode 2 for the measurement of the electrical conductivity in the same manufacturing process.

In the electromagnetic flow meter 100 according to the embodiment, since the magnetic excitation current Iex and the pulse V1 hardly interfere with each other by setting the frequency f1 of the pulse V1 as the AC signal to 100 times or more than the magnetic excitation frequency fex, it is possible to further prevent the decrease of the measurement precision and the measurement stability of the flow rate and the electrical conductivity.

As described above, it is possible to further improve the measurement precision and the reproducibility of the electrical conductivity of the measurement target fluid (resistor Rb) by setting the frequency f1 of the pulse V1 input to the non-contact electrode 2 through the resistor R1 to the value within the range expressed by Equation (7).

Even in a case where a noise including frequency components of the pulse V1 is superimposed on the flow rate signal VF, it is possible to remove the noise by providing filters (low-pass filter circuit 131 and high-pass filter circuit 132) for attenuating the frequency components corresponding to the pulse V1 in the amplifying circuit 13 for realizing the flow rate measurement function. As a result, since it is possible to further prevent the decrease of the measurement precision and the measurement stability of the flow rate and to dispose the detecting electrodes 11 and 12 and the non-contact electrode 2 close to each other, it is possible to further miniaturize the electromagnetic flow meter.

Since the electromagnetic flow meter 100 comprises the empty state determining portion 64 that determines the presence or absence of the fluid in the measurement tube 1 based on the electrical conductivity of the fluid calculated by the electrical conductivity calculating portion 62, it is possible to more reliably perform the determination of the empty state of the measurement tube 1.

For example, as a determination method of the empty state in the capacitive type electromagnetic flow meter in the related art, there is a known technique (for example, refer to PTL 2) that performs the determination of the empty state of a measurement tube by comparing an ideal waveform of a flow rate signal when a fluid normally flows in the measurement tube with an actually measured flow rate signal. However, since the related art is an indirect method of determining that the measurement tube is empty in a case where a flow rate signal is different from the waveform during normal time, it cannot be said that the detection accuracy of the empty state is high. On the contrary, in the electromagnetic flow meter 100 according to the embodiment 1, since it is determined whether there is a fluid in the measurement tube based on the electrical conductivity, it is possible to improve determination accuracy of the empty state as compared with the indirect method in the related art.

With the electromagnetic flow meter 100 according to the embodiment, since one electrode (non-contact electrode 2) of the two electrodes necessary for the measurement of the electrical conductivity described above is not in contact with the measurement target fluid, it is possible to suppress the measurement error due to the adhesion of the foreign matter or the corrosion of the electrode as compared with the two-electrode type electrical conductivity meter in the related art, in which the two electrodes are in contact with the measurement target fluid at the same time.

In the two-electrode type electrical conductivity meter in the related art, expensive platinum black is used for the two electrodes used for the measurement of the electrical conductivity in order to prevent the adhesion of the foreign matter or the corrosion of the electrode. However, in the electromagnetic flow meter 100 according to the embodiment, since there is no need to use the platinum black at least for the non-contact electrode 2, it is possible to further suppress the manufacturing costs of the electromagnetic flow meter having the electrical conductivity measurement function.

It is possible to widen the area in contact with the measurement target fluid of the contact electrode 3 by using the joint 3A formed of a metal for connecting to the external pipe as the contact electrode 3. According to this, as described above, even in the case where the adhesion of the foreign matter or the corrosion occurs in the contact electrode 3, since the area of the portion in which the adhesion of the foreign matter or the corrosion occurs is relatively small with respect to the entire contact area of the contact electrode 3, it is possible to further reduce the measurement error due to the adhesion of the foreign matter or the corrosion of the electrode.

In the case of connecting the metal pipe to the joint 3A, since the metal pipe is connected to the common potential Vcom through the joint 3A, it is possible to regard not only the joint 3A, but also the metal pipe as the contact electrode 3. According to this, since the contact area of the contact electrode 3 further increases and the area of the portion in which the adhesion of the foreign matter or the corrosion occurs is relatively small with respect to the entire contact area of the contact electrode 3, it is possible to further reduce the measurement error due to the adhesion of the foreign matter or the corrosion of the electrode.

Even in the case where the metal pipe is used, since the joint 3A as the contact electrode 3 and the metal pipe are at the same electropotential (common potential Vcom=0V), measurement error in the electrical conductivity due to the current flowing into the metal pipe does not occur.

Since the contact electrode 3 is connected to the common potential Vcom (=0 V), even in the case where the metal pipe is used, it is possible to prevent the metal pipe as an antenna from radiating the electromagnetic wave noise around the periphery.

As illustrated in FIGS. 10A and 10B, it is possible to reduce the electromagnetic wave noise radiated from the non-contact electrode 2 to the outside of the casing 20 as described above by disposing the shield cover 21 formed of a metal to face at least a part of the non-contact electrode 2.

<<Extension of Embodiment>>

The invention made by the present inventor is described in detail based on the embodiment. However, it goes without saying that the present invention is not limited thereto and various modifications can be made without departing from the gist thereof.

For example, in the embodiment, as the filter for removing the frequency components of the pulse V1 included in the flow rate signal, the case where the low-pass filter circuit 131 and the high-pass filter circuit 132 are provided is exemplified, but any one of the low-pass filter circuit 131 and the high-pass filter circuit 132 may be provided.

The low-pass filter circuit 131 and the high-pass filter circuit 132 are not limited to the circuit configuration illustrated in FIG. 1, and may have circuit configurations that can realize target filter characteristics.

In the embodiment, the configuration illustrated in FIG. 8 is exemplified as the realization example of the electromagnetic flow meter 100, but the invention is not limited thereto.

In the above embodiment, the invention is not limited to the circuit configuration example illustrated in FIG. 1 as long as the AC signal generation portion 4 and the voltage detecting portion 5 can exhibit the functions.

Similar to the data processing controlling portion 6, the analog/digital converting portion 7, the clock signal generating portion 8, and a part of the signal detecting portion 14 may be realized by the function of the program processing device, such as the microcontroller.

DESCRIPTION OF REFERENCE NUMERALS AND SIGNS

100: electromagnetic flow meter; 1: measurement tube; 2: non-contact electrode (third electrode); 3: contact electrode (fourth electrode); 3A and 3B: joint; 4: AC signal generation portion; 5: voltage detecting portion; 6: data processing controlling portion; 7: analog/digital converting portion; 8: clock signal generating portion; 9: setting/displaying portion; 10: analog outputting portion: 11: the detecting electrode (first electrode); 12: the detecting electrode (second electrode); 13: amplifying circuit; 14: signal detecting portion; 15: magnetic excitation circuit; 20: casing; 21: shield cover; 22: printed circuit board; 23: metal solid pattern; 51 and 52: sample hold circuit; 61: reference clock generating portion; 62: electrical conductivity calculating portion; 63: flow rate calculation portion; 64: empty state determining portion; 65: magnetic excitation controlling portion; 200, 201, and 202: equivalent circuit; 91: operating button; 92: display device; Lex: magnetic excitation coil; Iex: magnetic excitation current; SW1, SW2, and SW3: switch; U1 and U5: buffer amplifier; U2 and U3: preamplifier; U4: differential amplifying circuit: 131: low-pass filter circuit; 132: high-pass filter circuit; CLK0: reference clock signal; CLK1, CLKp, and CLKn: clock signal; V1: pulse (signal source); V2 and V2b: signal; Vcom: common potential; VH and VL: voltage of signal V2; VF: the flow rate signal; Tp: period in which pulse V1 has first polarity; Tn: period in which pulse V1 has second polarity; Ra: polarization resistance; Rb: fluid resistance; R1: resistor; C1, C2, Cb, and Cc: capacitor; Ca: polarization capacitance

The invention claimed is:
1. An electromagnetic flow meter comprising:
   a measurement tube which is formed of an electrical insulation material and through which a measurement target fluid flows;
   a magnetic excitation coil which is disposed outside the measurement tube and generates a magnetic field according to a supplied AC current having a first frequency;
   a first electrode and a second electrode which are provided on an outer peripheral surface of the measurement tube and are disposed opposite to each other in a direction perpendicular to the magnetic field generated from the magnetic excitation coil;
   an amplifying circuit that operates with a common potential as a reference and outputs a signal obtained by amplifying an electromotive force generated between the first electrode and the second electrode;
   a flow rate calculation portion that calculates a flow rate of the measurement target fluid based on a signal output from the amplifying circuit;
   a third electrode which is formed on the outer peripheral surface of the measurement tube to be separated from the first electrode and the second electrode;
   a fourth electrode which is connected to the common potential and is in contact with the measurement target fluid;
   a resistor of which one end is connected to the third electrode;
   an AC signal generator connected to another end of the resistor, the AC signal generator being adapted to generate an AC signal having a second frequency that is different from the first frequency;
   a voltage detecting circuit that measures voltages of a signal generated in the third electrode while the AC signal is generated at and input to the another end of the resistor; and
   an electrical conductivity calculating portion that calculates an electrical conductivity of the measurement target fluid based on an amplitude of the voltages measured by the voltage detecting circuit.

2. The electromagnetic flow meter according to claim 1, wherein the second frequency of the AC signal is at least 100 times the first frequency of the AC current supplied to the magnetic excitation coil.

3. The electromagnetic flow meter according to claim 2, wherein the amplifying circuit comprises filters for attenuating frequency components corresponding to the AC signal which are included in the signal obtained by amplifying the electromotive force.

4. The electromagnetic flow meter according to claim 3, further comprising:
   a determining portion that determines a presence or absence of the measurement target fluid in the measurement tube based on the electrical conductivity of the measurement target fluid calculated by the electrical conductivity calculating portion.

5. The electromagnetic flow meter according to claim 4, wherein the second frequency f1 of the AC signal input to the resistor satisfies a condition expressed by an equation (A) when a resistance value of the measurement target fluid is Rb, and capacitance between the measurement target fluid flowing in the measurement tube and the third electrode is Cb

[Math. 1]
$$\frac{1}{2 \times \pi \times Cb \times Rb} \leq f1 \leq \frac{10}{2 \times \pi \times Cb \times Rb} \quad (A)$$

6. The electromagnetic flow meter according to claim 5, wherein the voltage detecting circuit comprises
   a first sample hold circuit for sampling and holding a first voltage of the third electrode in a first period in which the AC signal has a first polarity, and
   a second sample hold circuit for sampling and holding a second voltage of the third electrode in a second period in which the AC signal has a second polarity opposite to the first polarity, and
   wherein the electrical conductivity calculating portion calculates the electrical conductivity of the measurement target fluid based on the first voltage sampled by the first sample hold circuit and the second voltage sampled by the second sample hold circuit.

7. The electromagnetic flow meter according to claim 6, wherein the fourth electrode is a pipe-shaped joint formed of a metal, of which one end is connected to the measurement tube and another end is connectable to an external pipe.

8. The electromagnetic flow meter according to claim 7, further comprising:
   a shield cover which is formed of a metal and disposed to face at least a part of the third electrode.

9. The electromagnetic flow meter according to claim 2, further comprising:
   a determining portion that determines a presence or absence of the measurement target fluid in the measurement tube based on the electrical conductivity of the measurement target fluid calculated by the electrical conductivity calculating portion.

10. The electromagnetic flow meter according to claim 2, wherein the second frequency f1 of the AC signal input to the resistor satisfies a condition expressed by an equation (A) when a resistance value of the measurement target fluid is Rb, and capacitance between the measurement target fluid flowing in the measurement tube and the third electrode is Cb

[Math. 1]

$$\frac{1}{2 \times \pi \times Cb \times Rb} \leq f1 \leq \frac{10}{2 \times \pi \times Cb \times Rb} \quad (A)$$

11. The electromagnetic flow meter according to claim 2, wherein the voltage detecting circuit comprises
a first sample hold circuit for sampling and holding a first voltage of the third electrode in a first period in which the AC signal has a first polarity, and
a second sample hold circuit for sampling and holding a second voltage of the third electrode in a second period in which the AC signal has a second polarity opposite to the first polarity, and
wherein the electrical conductivity calculating portion calculates the electrical conductivity of the measurement target fluid based on the first voltage sampled by the first sample hold circuit and the second voltage sampled by the second sample hold circuit.

12. The electromagnetic flow meter according to claim 2, wherein the fourth electrode is a pipe-shaped joint formed of a metal, of which one end is connected to the measurement tube and another end is connectable to an external pipe.

13. The electromagnetic flow meter according to claim 2, further comprising:
a shield cover which is formed of a metal and disposed to face at least a part of the third electrode.

14. The electromagnetic flow meter according to claim 1, wherein the amplifying circuit comprises filters for attenuating frequency components corresponding to the AC signal which are included in the signal obtained by amplifying the electromotive force.

15. The electromagnetic flow meter according to claim 1, further comprising:
a determining portion that determines a presence or absence of the measurement target fluid in the measurement tube based on the electrical conductivity of the measurement target fluid calculated by the electrical conductivity calculating portion.

16. The electromagnetic flow meter according to claim 1, wherein the second frequency f1 of the AC signal input to the resistor satisfies a condition expressed by an equation (A) when a resistance value of the measurement target fluid is Rb, and capacitance between the measurement target fluid flowing in the measurement tube and the third electrode is Cb,

[Math. 1]

$$\frac{1}{2 \times \pi \times Cb \times Rb} \leq f1 \leq \frac{10}{2 \times \pi \times Cb \times Rb} \quad (A)$$

17. The electromagnetic flow meter according to claim 1, wherein the voltage detecting circuit comprises
a first sample hold circuit for sampling and holding a first voltage of the third electrode in a first period in which the AC signal has a first polarity, and
a second sample hold circuit for sampling and holding a second voltage of the third electrode in a second period in which the AC signal has a second polarity opposite to the first polarity, and
wherein the electrical conductivity calculating portion calculates the electrical conductivity of the measurement target fluid based on the first voltage sampled by the first sample hold circuit and the second voltage sampled by the second sample hold circuit.

18. The electromagnetic flow meter according to claim 1, wherein the fourth electrode is a pipe-shaped joint formed of a metal, of which one end is connected to the measurement tube and another end is connectable to an external pipe.

19. The electromagnetic flow meter according to claim 1, further comprising:
a shield cover which is formed of a metal and disposed to face at least a part of the third electrode.

* * * * *